United States Patent [19]

Fowlkes et al.

[11] Patent Number: 4,868,335

[45] Date of Patent: Sep. 19, 1989

[54] SEPARATION OF MONO-N-HEXYLAMINE-WATER AZEOTROPE

[75] Inventors: Robert L. Fowlkes, Milton; Lewis S. Forester; George D. Cooper, both of Pensacola, all of Fla.

[73] Assignee: Air Products and Chemicals, Inc., Allentown, Pa.

[21] Appl. No.: 141,645

[22] Filed: Jan. 6, 1988

[51] Int. Cl.[4] .............................................. C07C 85/26
[52] U.S. Cl. .................................... 564/497; 564/498; 564/499; 203/49
[58] Field of Search ...................... 564/497, 499, 498; 203/49

[56] References Cited

U.S. PATENT DOCUMENTS

| | | | |
|---|---|---|---|
| 2,695,267 | 11/1954 | Challis | 564/498 |
| 3,433,788 | 3/1969 | Somekh et al. | 564/497 |
| 4,398,041 | 8/1983 | Cochran et al. | 564/479 |

OTHER PUBLICATIONS

Kirk-Othmer, "Encyclopedia of Chemical Technology", vol. 2, 2nd ed., 1971, p. 106.

The Condensed Chemical Dictionary, 7th ed., Arthur & Elizabeth Rose.

*Primary Examiner*—Glennon H. Hollrah
*Assistant Examiner*—Ba Trinh
*Attorney, Agent, or Firm*—Russell L. Brewer; James C. Simmons; William F. Marsh

[57] ABSTRACT

This invention relates to a process for separating mono-n-hexylamine from water and particularly to an improvement in a process for the recovery of mono-n-hexylamine from the reaction of n-hexanol with ammonia under amination conditions. In this process water is produced as a by-product and in the separation process an azeotrope is formed which comprises about 49% water and 51% hexylamine. The process for enhancing separation of the azeotrope of mono-n-hexylamine and water comprises contacting the azeotrope of mono-n-hexylamine and water with di-n-hexylamine or with a mixture of di-n-hexylamine and tri-n-hexylamine in sufficient amount to reduce the solubility of mono-n-hexylamine in water thus forming an organic phase and an aqueous phase which can be separated by simple techniques, e.g., decanting.

3 Claims, No Drawings

SEPARATION OF MONO-N-HEXYLAMINE-WATER AZEOTROPE

TECHNICAL FIELD

This invention relates to the separation of mono-n-hexylamine from mono-n-hexylamine-water azeotrope.

BACKGROUND OF THE INVENTION

In the conventional manufacture of mono-n-hexylamine, n-hexanol is contacted with ammonia under amination conditions to produce n-hexylamine and by-product water. One of the problems in the recovery of the hexylamine from the reaction mixture is that an azeotrope consisting of about 49% water and 51% hexylamine is formed and thus creates a problem in the recovery of the n-hexylamine from the reaction product.

As is known there are many procedures for breaking azeotropes and effect the separation of various components. For example one may adjust pressure or contact the azeotrope with another compound which forms an azeotrope with one of the compounds in the mixture. In the case of organics and water, one often may add a hydrocarbon to aid in the separation.

SUMMARY OF THE INVENTION

This invention relates to an improved process for separating an azeotrope of mono-n-hexylamine and water. The improvement comprises contacting the azeotropic mixture of mono-n-hexylamine and water with di-n-hexylamine or a mixture of di-n-hexylamine in sufficient amount to reduce the solubility in water thus forming an organic phase rich in hexylamine and an aqueous phase having reduced levels of hexylamines. These phases can be separated by decanting. The di-n-hexylamine can then be separated from the mono-n-hexylamine by distillation.

DETAILED DESCRIPTION OF THE INVENTION

In the manufacture of mono-n-hexylamine the corresponding alcohol, mono-n-hexanol, is contacted with ammonia in the presence of a catalyst such as cobalt on silica or cobalt on alumina. In this catalytic process water is formed as a by-product. Conventionally in the separation of alkylamines from the reaction product the reaction mixture is distilled and the amine recovered. However, in the case of mono-n-hexylamine an azeotrope is formed with the water which prevents separation by distillation.

The azeotrope which consists of about 49% mono-n-hexylamine and 51% water, on a weight basis, can be separated by adding di-n-hexylamine to the reaction product and preferably a mixture of 6 to 9 parts di-n-hexylamine and 1 to 4 parts tri-n-hexylamine total amine per 10 parts mixture to the reaction product. Di-n-hexylamine or the mixture is added in an amount of from about 50 to 500% preferably 75–125% by weight of the azeotrope and results in a reduction in the solubility of the mono-n-hexylamine in water to produce a water rich phase and an organic rich phase consisting largely of the mono-n-hexylamine and the additive di-n-hexylamine or di-n-hexylamine and tri-n-hexylamine components if added. More particularly at temperatures from about 20° to 100° C. a three component system of water, mono-n-hexylamine and di-n-hexylamine wherein the hexylamine components are present in substantially equal proportions separates into two phases with the organic phase containing about 9 parts water, 46 parts mono and 45 parts di-n-hexylamine by weight while the aqueous phase contains about 95 parts water 4 parts mono-n-hexylamine and 1 part di-n-hexylamine. When less than 50% di-n-hexylamine or mixture of hexylamine is used the separation may not be as complete as desired. When more than 125% is used, then handling problems may occur and no significant advantages achieved.

The following examples are provided to illustrate various embodiments of the invention and are not intended to be restrictive.

EXAMPLE 1

Approximately 100 parts by weight portion of a feed azeotropic mixture consisting of 49% water and 51% mono-n-hexylamine was charged to a mixer wherein it is contacted with 100 parts of di-n-hexylamine to produce 200 parts of a stream containing 26% water, 24% mono-n-hexylamine and 50% di-n-hexylamine. The temperature was then adjusted to 100° C. and charged to a decanter. The mixture in the decanter was allowed to separate forming an top organic phase fraction rich in amines and containing approximately 5 parts water, 30 parts mono-n-hexylamine and 65 parts di-n-hexylamine. A bottoms fraction consisting of 3 parts mono-n-hexylamine, 1 part di-n-hexylamine and less than 96 parts water was formed and removed from the bottom of the decanter. The top layer was charged to a distillation column generating an overhead which was sent to the mixer and a bottoms devoid of water consisting of 31% mono-n-hexylamine and 69% di-n-hexylamine. The bottoms fraction from the decanter was subjected to further distillation to recover the dissolved amines. The energy requirements for separating the mono-n-hexylamine from water was 273 BTU's /lb of mono-n-hexylamine separated.

This example shows the effectiveness of di-n-hexylamine in the breaking of an azeotropic mixture of mono-n-hexylamine and water to effect separation with at low energy requirements.

EXAMPLE 2

The procedure of Example 1 was repeated except that the contents of the di-n-hexylamine-azeotrope mixture was heated to only 25° C. On separtion the top layer contained 29 parts mono-n-hexylamine, 64 parts di-n-hexylamine, and 7 parts water. The bottoms part contained 3 parts mono-n-hexylamine, 1 part di-n-hexylamine and 96 parts water.

Based upon these results it can be seen slightly more water is present in the top layer submitted to the distillation column when the extraction is carried out at the lower temperature. Thus, slightly higher energy requirements are necessary for this embodiment.

EXAMPLE 3

The procedure of Example 1 was repeated except that 100 parts by weight n-hexanol were substituted for 100% di-n-hexylamine. The organic phase from the decanter contained approximately 12 parts water, 28% mono-n-hexylamine and 59% n-hexanol. The bottomed water containing fraction water from the decanter contained 96% water, 3% mono-n-hexylamine and 1% mono-n-hexanol. The energy requirement for this embodiment was 910 BTU's/lb of mono-n-hexylamine separated.

EXAMPLE 4

The procedure of Example 1 was repeated except that 50 parts di-n-hexylamine was substituted for the 100 parts di-n-hexylamine. The top organic fraction contained 51 parts mono-n-hexylamine, 35 parts di-n-hexylamine and 14 parts water. The bottoms fraction contained 6 parts mono-n-hexylamine, 1 part di-n-hexylamine and 93 parts water.

Although the addition of the lesser quantity of di-n-hexylamine was effective for breaking the azeotrope it was not as effective as when higher levels of di-n-hexylamine were used.

EXAMPLE 5

Comparison Example

The procedure of Example 1 was repeated except that hexane was substituted for the di-n-hexylamine and the azeotrope and hexane were changed to the column. Further, the hexane was added in an amount to provide sufficient volume for operation of the decanter. This necessitated about 1200–1300 parts hexane per 100 parts azeotrope being charged to the distillation column. This was not a problem when the amine was added to the decanter as in Example 1. A bottom fraction was obtained from the column and consisted of 100 parts mono-n-hexylamine essentially free of water and hexane. The overheads from the column was sent to the decanter. A top layer was generated and returned to the distillation column as reflux and contained approximately 5.6% water and 94.4% hexane. The bottom layer of the decanter consisted of 99.6% water and was sewered. The energy requirements for this embodiment was calculated and found to be 3308 BTU's/lb of mono-n-hexylamine separated.

The example shows that hexane is effective for breaking the azeotrope of mono-n-hexylamine and water but it is not as efficient as di-n-hexylamine.

What is claimed is:

1. A process for separating an azeotropic mixture of mono-n-hexylamine and water, which comprises:

contacting the azeotrope with sufficient di-n-hexylamine to form an aqueous phase consisting predominantly of water and an organic phase consisting predominantly of mono-n-hexylamine and di-n-hexylamine;

separating the organic phase from the aqueous phase; and, separating the mono-n-hexylamine from the di-n-hexylamine.

2. The process of claim 1 wherein tri-n-hexylamine is added in combination with di-n-hexylamine to the azeotrope in an amount to provide from 1–4 parts tri-n-hexylamine and 6–9 parts di-n-hexylamine per 10 parts by weight total amine to the azeotrope.

3. The process of claim 1 wherein the di-n-hexylamine is added in amount of from about 75 to 125 parts by weight per part of mono-n-hexylamine-water azeotrope.

* * * * *